United States Patent
Watanabe et al.

(10) Patent No.: US 6,346,507 B1
(45) Date of Patent: Feb. 12, 2002

(54) LIQUID CRYSTAL COMPOSITION AND COSMETIC PREPARATION

(75) Inventors: Kei Watanabe; Fumiaki Matsuzaki; Toshio Yanaki, all of Kanagawa; Kazuyoshi Nakamura, Niigata; Natsuko Fujii, Toyama, all of (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/517,429

(22) Filed: Mar. 2, 2000

(30) Foreign Application Priority Data

Mar. 4, 1999 (JP) ............................... 11-057281

(51) Int. Cl.7 ...................... C11D 17/00; C11D 17/08; C11D 3/38
(52) U.S. Cl. .................. 510/343; 510/417; 510/466
(58) Field of Search ................... 510/136, 130, 510/137, 340, 343, 413, 417, 466

(56) References Cited

FOREIGN PATENT DOCUMENTS

| EP | 0 217 105 A2 | 4/1987 |
|----|--------------|--------|
| JP | 59046123 A | 3/1984 |
| JP | 62053910 A | 3/1987 |
| JP | 62096585 A | 5/1987 |
| JP | 01252664 A | 10/1989 |
| JP | 04348162 | 12/1992 |
| JP | 06048916 | 2/1994 |
| JP | H6-192036 | 7/1994 |
| JP | 07291825 | * 11/1995 |
| JP | 08127512 | 5/1996 |
| JP | 09175936 | 7/1997 |

OTHER PUBLICATIONS

Japanese Patent Office, Patent Abstracts of Japan, Publication No. 07291825, Date of Publication: Nov. 7, 1995, Application No.: 06091314, Date of Application: Apr. 28, 1994. vol. 1996, No. 03.

* cited by examiner

Primary Examiner—Mark Kopec
Assistant Examiner—John M Petruncio
(74) Attorney, Agent, or Firm—Snider & Associates; Ronald R. Snider

(57) ABSTRACT

In order to provide a liquid crystal composition and a cosmetic preparation, which is favorable in adaptation to skin and gives smooth feeling in case of using as a skin care product, and which is favorable in adaptation to makeup and has high makeup removing effect in case of using as a make-up remover, and which is favorable in adaptation to hair and has favorable feeling of use to provide glossiness to hair in case of using as a hair care product, a cosmetic preparation of the present invention comprises (A) 10 to 60 wt % of a nonionic surfactant, (B) 1 to 50 wt % in all of one or more of a water-soluble substance having a hydroxyl group, (C) 1 to 70 wt % of a silicone oil, and (D) 10 to 60 wt % of water and has a liquid crystal phase and/or an isotropic surfactant continuous phase.

13 Claims, No Drawings

LIQUID CRYSTAL COMPOSITION AND COSMETIC PREPARATION

RELATED APPLICATIONS

This application claims the priority of Japanese Patent Application No. 11-57281 filed on Mar. 4, 1999, which is incorporated herein by reference.

FIELD OF THE INVENTION

The present invention relates to a liquid crystal composition and a cosmetic preparation, and, in particular, to an improvement in usability of the cosmetic preparation and effect for removing makeup in case of using those as a make-up remover.

BACKGROUND OF THE INVENTION

Skin care creams, milky lotions, essences, massage creams and the like which aim at moisturizing skin comprise water-soluble and oil-soluble ingredients. A small amount of amphiphathic substances such as nonionic surfactants are used for the purpose of emulsifying these ingredients homogeneously. Make-up removers which aim at removing base makeup such as foundation or point makeup such as lipstick comprise oily ingredients for the purpose of dissolving and dispersing makeup. Among these make-up removers, there are O/W and W/O emulsion type make-up removers which are emulsified with amphiphathic substance, and oil type make-up remover, which mixes several kinds of oily ingredients. Further, in recent, there is aqueous type make-up remover, which comprises a large amount of surfactant having middle level of HLB without oily ingredient.

However, in case of skin care products, water and oils emitted due to demulsification tend to separate in the process of making them adapt to skin. Accordingly, there is restriction on the amount of surfactant and the kind of oily ingredient in order to ameliorate skin adaptation. There also is restriction on the kind of surfactant in case of compounding silicon oils that provide smooth feeling. In case of O/W emulsion type make-up remover, there is a problem that adaptation to skin is slow because adaptation to makeup occurs after coalescence of emulsion particle. Also, in case of W/O emulsion type or oil type make-up remover, there is almost no problem in adaptation to or removal of makeup. However, there is a great problems on the feeling of use, e.g., remain of oiliness after wiping off with a tissue paper or washing face. In case of aqueous type make-up remover, there is absolutely no oiliness, while there is a problem that effect for removing makeup is not sufficient. For the purpose of resolving such problems on make-up remover, an art using liquid crystal one-phase system which uses polar oils or paraffins is shown in such as Japanese Examined Patent Publication Nos. 1-53845 and 3-71475. In recent year, however, cosmetic durability of various make-up preparations has been ameliorated largely. In the present circumstances, adaptation to makeup and effect for removing makeup are not always sufficient in case of using polar oil or paraffins. Further, in case of using liquid crystal one-phase system as a make-up remover as it is, there remains the problem that heavy feeling is caused at application because liquid crystal structure is somewhat difficult to break.

SUMMARY OF THE INVENTION

The present invention is achieved in view of the foregoing prior art, an object of the present invention is to provide a liquid crystal composition and a cosmetic preparation which is favorable in adaptation to skin and gives smooth feeling in the case where both are used as a skin care product. Further, an object of the present invention is to provide a liquid crystal composition and a cosmetic preparation which is favorable in adaptation to makeup and has high makeup removing effect in the case where both are used as a make-up remover. Still further, an object of the present invention is to provide a liquid crystal composition and a cosmetic preparation which is favorable in adaptation to hair and has favorable feeling of use to provide glossiness to hair in the case where both are used as a hair care product.

As the result of diligent studies of the present inventors in view of the above-mentioned circumstances, it has been found that a cosmetic preparation which comprises 10to 60 wt % of a nonionic surfactant, 1 to 50 wt % in all of one or more of a water-soluble substance having a hydroxyl group, 1 to 70 wt % of a silicone oil, and 10 to 60 wt % of water, and has a liquid crystal phase and/or an isotropic surfactant continuous phase can resolve the above-mentioned problem. Further, it has been found that: a cosmetic preparation, which is favorable in adaptation to skin and gives smooth feeling in the case where the cosmetic preparation is used as a skin care product; a cosmetic preparation, which is favorable in adaptation to makeup and has high makeup removing effect in the case where the cosmetic preparation is used as a make-up remover; and a cosmetic preparation, which is favorable in adaptation to hair and has favorable feeling of use to provide glossiness to hair in the case where the cosmetic preparation is used as a hair care product. Accordingly the present invention has been accomplished.

Namely, a liquid crystal composition of the present invention comprises: (a) 10 to 60 wt % of a nonionic surfactant; (b) 1 to 50 wt % in all of one or more of a water-soluble substance having a hydroxyl group; (c) 1 to 70 wt % of a silicone oil; and (d) 10 to 60 wt % of water.

Also, a cosmetic preparation of the present invention comprises: (A) 10 to 60 wt % of a nonionic surfactant; (B) 1 to 50 wt % in all of one or more of a water-soluble substance having a hydroxyl group; (C) 1 to 70 wt % of a silicone oil; and (D) 10 to 60 wt % of water, wherein said cosmetic preparation has a liquid crystal phase and/or an isotropic surfactant continuous phase.

Also, the cosmetic preparation of the present invention is applied to skin.

Also, the cosmetic preparation of the present invention removes makeup.

Also, it is preferable that at least one of the water-soluble substance having a hydroxyl group is a water-soluble monohydric alcohol.

Also, it is preferable that at least one of the water-soluble substance having a hydroxyl group is a water-soluble polyhydric alcohol.

Also, it is preferable that a ratio of the nonionic surfactant and water (nonionic surfactant/water) is 0.5 to 4.

Also, it is preferable that a cosmetic preparation of the present invention is a one-phase system which is any one of a gel phase, a liquid crystal phase or an isotropic surfactant continuous phase those are formed by associating a surfactant or a coexisting-phase system of any one of the gel phase, the liquid crystal phase or the isotropic surfactant continuous phase and the other phases.

Also, it is preferable that the cosmetic preparation of the present invention is the one-phase system of the liquid crystal phase or the coexisting-phase system of plural phases including the liquid crystal phase.

Also, it is preferable that the cosmetic preparation of the present invention is the coexisting-phase system of plural phases including the liquid crystal phase.

Also, it is preferable that the cosmetic preparation of the present invention is the one-phase system of the isotropic surfactant continuous phase or the coexisting-phase system of plural phases including the isotropic surfactant continuous phase.

BEST MODE FOR CARRYING OUT THE INVENTION

As an example of the nonionic surfactant which is useful in the present invention, sorbitan fatty acid ester, polyoxyethylene sorbitan fatty acid ester, glycerin fatty acid ester, ethylene oxide derivatives of glycerin fatty acid ester, polyglycerin fatty acid ester, propylene glycol fatty acid ester, ethylene oxide derivatives of propylene glycol fatty acid ester, polyethylene glycol fatty acid ester, polyethylene glycol alkyl ether, polyethylene glycol alkyl phenyl ether, polyethylene glycol castor oil derivatives, and polyethylene glycol hydrogenated castor oil derivatives are cited. The amount of the nonionic surfactant is preferably 10 to 60 wt % and more preferably 15 to 50 wt %. Adaptation to skin, makeup or hair is not sufficient in the case where the amount of the nonionic surfactant is less than 10 wt %. In case of compounding the nonionic surfactant more than 60 wt %, it is not preferable because it gives sticky feeling.

Also, as an example of the water-soluble substance having a hydroxyl group which is useful in the present invention, water-soluble monohydric alcohols and water-soluble polyhydric alcohols are cited. Examples of the water-soluble monohydric alcohol include ethanol, propanol, isopropanol, butanol and isobutanol. Among of these water-soluble monohydric alcohols, ethanol is particularly preferable. Examples of the water-soluble polyhydric alcohol include propylene glycol, 1,3-butylene glycol, dipropylene glycol, glycerin, diglycerin, polyglycerin, erythritol, pentaerythritol, sorbitan, glucose, sorbitol, maltitol, trehalose, and polyethylene glycol. Among of these water-soluble polyhydric alcohols, 1,3-butylene glycol, dipropylene glycol and glycerin are particularly preferable. These water-soluble substances having a hydroxyl group may be used singly or as mixtures of two or more of them. Though the amount of the water-soluble substance depends on viscosity and hardness of the objective cosmetic preparation, it is desirable to compound the water-soluble substance within the range of 1 to 50 wt %. Adaptation to skin, makeup or hair is not sufficient in the case where the amount of the water-soluble substance is less than 1 wt %. In case of compounding the water-soluble substance more than 50 wt % in total, undesirable feeling of use, i.e., stickiness feeling in case of using polyhydric alcohols and smart feeling in case of using monohydric alcohols, may be provided.

As an example of the silicone oil which is useful in the present invention include chain silicones such as dimethyl polysiloxane, methyl phenyl polysiloxane, and methyl hydrogen polysiloxane and cyclic silicones such as octamethylcyclotetrasiloxane, decamethylcyclopentasiloxane, and dodecamethylcyclohexanesiloxane. Among of these silicone oils, dimethylpolysiloxane, octamethylcyclotetrasiloxane and decamethylcyclopentasiloxane are preferable and octamethylcyclotetrasiloxane and decamethylcyclopentasiloxane are particularly preferable. These silicone oils may be used singly or as mixtures of two or more of them. The amount of the silicone oil is 1 to 70 wt %. Adaptation to skin, makeup or hair is not sufficient in the case where the amount of the silicone oil is less than 1 wt %. In case of compounding the silicone oil more than 70 wt %, it is not desirable because the effect by including silicone oil is not improved so much.

The amount of water can be properly set according to the purpose of use. The amount of water is preferably 10 to 60 wt %. It is desirable that a ratio of the nonionic surfactant and water (nonionic surfactant/water) in this time is 0.5 to 4. Adaptation to skin, makeup or hair is not sufficient in the case where the ratio is less than 0.5. If the ratio is more than 4, it is undesirable because sticky feeling of use is provided.

The cosmetic preparation of the present invention may be prepared in one phase region which is a phase having associated form of the liquid crystal phase, the isotropic surfactant continuous phase and the like or in the composition of coexisting-phase system of a phase having associated form of the liquid crystal phase, the isotropic surfactant continuous phase and the like and the other phases. One-phase system of liquid crystal phase or isotropic surfactant continuous phase and the coexisting-phase system of liquid crystal phase and the other phases are preferable. As an example of the coexisting-phase system of liquid crystal phase and the other phases, O/LC (oil is dispersed into liquid crystal phase, same in the following), LC/O, W/LC, LC/W, D/LC, LC/D and the like can be cited. In here, LC, D, O, and W represents liquid crystal phase, isotropic surfactant continuous phase, oil phase or micelle oil solution phase, and water phase or water solution phase, respectively. O/LC is particularly preferable.

It is possible to add various ingredients, which can be used for the general cosmetics into the cosmetic preparation of the present invention within the range that stability of the cosmetic preparation is not spoiled.

As an example of the liquid fats and oils, linseed oil, camellia oil, macademia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, triglycerin, glyceryl trioctanoate, glyceryl triisopalmitate, and the like are cited.

As an example of the ester oil, cetyl octanoate, hexyl laurate, isopropyl myristate, octyl palmitate, isocetyl stearate, isopropyl isostearate, octyl isopalmitate, isodecyl oleate, glyceryl tri-2-ethylhexanoate, pentaerythritol tetra-2-ethylhexanoate, di-(2-ethylhexyl) succinate, diethyl sebacate, and the like are cited.

As an example of the hydrocarbon oil, liquid paraffin, squalane, squalene, paraffin, isoparaffin, ceresine, and the like are cited.

As an example of the water-soluble polymer: vegetable polymers such as arabic gum, carageenan, pectin, agar, quince seed (*Cydonia vulgaris* Pers), starch and algae colloid (seaweed extract); microorganism polymers such as dextran and pullulan; animal polymers such as collagen, casein, and gelatin; starch polymers such as carboxymethyl starch and methyl hydroxypropyl starch; alginic acid polymers such as sodium alginate; vinyl polymers such as carboxyvinyl polymer (such as CARBOPOL™); polymers of polyoxyethylene; polymers of polyoxyethylene polyoxypropylene copolymer; acrylic polymers such as sodium polyacrylate and polyacrylamide; and inorganic water-soluble polymers such as bentonite, aluminium magnesium silicate, and LAPONITE™ are cited.

As an example of the ultraviolet absorber: benzoic acid ultraviolet absorbers such as p-aminobenzoic acid; anthranilic acid ultraviolet absorbers such as methyl anthranilate;

salicylic acid ultraviolet absorbers such as octyl salicylate and phenyl salicylate; cinnamic acid ultraviolet absorbers such as isopropyl methoxycinnamate, octyl methoxycinnamate, and glyceryl octanoate di-p-methoxy cinnamate; benzophenone ultraviolet absorbers such as 2,4-dihydroxybenzophenone, 2-hydroxy-4-methoxybenzophenone, and 2-hydroxy-4-methoxy-benzophenone-5-sulfonic acid; and the other ultraviolet absorbers such as urocanic acid, 2-(2'-hydroxy-5'-methyl phenyl) benzotriazole, and 4-tert-butyl-4'-methoxy-dibenzoylmethane are cited.

As an example of the sequestering agent, sodium edetate, sodium metaphosphate, and phosphoric acid are cited.

As an example of the anti-oxidant, ascorbic acid, α-tocopherol, dibutyl hydroxy toluene, and butylhydroxyanisol are cited.

As an example of the medicament: Vitamins such as Vitamin A oil, retinol, retinol palmitate, inositol, pyridoxine hydrochloride, benzyl nicotinate, nicotinamide, dl-α-tocopheryl nicotinate, magnesium ascorbate phosphate, ascorbate 2-glucoside, Vitamin $D_2$ (ergocalciferol), dl-α-tocopherol 2-L ascorbate phosphate diester potassium, dl-α-tocopherol, dl-α-tocopheryl acetate, panthotenic acid, and biotin; hormones such as estradiol and ethinylestradiol; anti-inflammatory agents such as allantoin and azulene; whitening agents such as arbutin; astringents such as zinc oxide and tannic acid; refreshing agents such as L-menthol and camphor; and the other medicaments such as sulfur, lysozyme chloride, pyridoxine hydrochloride, and γ-oryzanol.

As an example of various extracts, houttuynia extract, phellodendron bark extract, sweet clover extract, white nettle extract, glycyrrhiza extract, paeony root extract, saponaria extract, sponge gourd extract, cinchona extract, saxifrage extract, sophora root extract, nuphar extract, fennel extract, primula extract, rose extract, rehmannia root extract, lemon extract, lithospermum root extract, aloe extract, calamus rhizome extract, eucalyptus extract, horsetail extract, sage extract, thyme extract, green tea extract, seaweed extract, cucumber extract, clove extract, raspberry extract, balm mint extract, ginseng extract, carrot extract, horse chestnut extract, peach extract, peach leaf extract, mulberry bark extract, cornflower extract, witch hazel extract, placental extract, thymus extract, and silk extract are cited.

The medicaments mentioned hereinbefore can be used in free state. Besides this formulation, the medicaments which are capable of forming salt can be used in the form of an acid or a salt of a base, while the medicaments having a carboxylic acid group can be used in the form of an ester thereof.

Further, as the occasion demands, suitable perfumes, coloring matters, and the like can be added to the cosmetic preparation of the present invention within the range that stability of the cosmetic preparation is not spoiled.

The cosmetic preparation of the present invention can be utilized for the whole possible cosmetics, e.g.,: skin care products such as moisture cream, moisture milky lotion, moisture lotion, massage cream, massage lotion, and essence; hair care products such as hair cream, hair lotion, and hair dressing; body care products such as sun screen, body cream, and body lotion; make-up products such as lipstick, mascara, eye liner, nail enamel, liquid foundation, and gel foundation; and washing products such as make-up remover, shampoo, rinse, and rinse-in-shampoo-type shampoo.

The present invention is explained according to examples in the following. The present invention, however, is not limited by these examples. Evaluation standards are explained before showing the composition of example. Three types of use test were conducted in evaluating the cosmetic preparation of the present invention.

Use Test of Make-Up Remover

Use test of make-up remover was conducted for ten persons of professional panel. Evaluation items are adaptation to makeup and oiliness feeling after removing makeup with washing.

<Evaluation Standard of Adaptation to Makeup>

○: 7 or more among 10 persons evaluated that adaptation to makeup was good.

Δ: 4 or more among 10 persons evaluated that adaptation to makeup was good.

X: 3 or less among 10 persons evaluated that adaptation to makeup was good.

<Evaluation Standard of Oiliness Feeling>

○: 7 or more among 10 persons evaluated favorably that there was no oiliness.

Δ: 4 or more among 10 persons evaluated favorably that there was no oiliness.

X: 3 or less among 10 persons evaluated favorably that there was no oiliness.

<Test for Effect of Make-Up Remover>

Make-up remover was adapted with makeup and makeup was removed from skin by wiping or washing. Then, makeup was further wiped off strongly by a tissue paper, which soaked a small amount of ethanol. Effect of make-up remover was judged from the amount of pigment and the like of makeup which were adhered to a tissue paper.

◎: Pigment was not observed on a tissue paper at all.

○: Pigment was slightly observed on a tissue paper.

Δ: Pigment was observed on a tissue paper

X : Pigment was obviously observed on a tissue paper.

As a result that the present inventors have studied the system of water/nonionic surfactant/water-soluble substance having hydroxyl group/silicone oil, it is found that a mixture of the nonionic surfactant and the water-soluble substance having a hydroxyl group, and the silicone oil are dissolved homogeneously at wide range and form a reversed micelle solution phase (indicated"reversed micelle·isotropic" hereafter) which is isotropic optically in case of compounding a small amount of water. On the contrary, it is found that a mixture of the nonionic surfactant and the water-soluble substance having a hydroxyl group, and the silicone oil form two-phases coexisting system (indicated"emulsification·isotropic" hereafter) in the case where the concentration of the mixture is thin. In proportion to addition of water to the reversed micelle solution, lamella liquid crystal comes to separate. Since a part having extremely high viscosity and transparent appearance exists in the region of lamella liquid crystal, the present inventors decide to call this"gel phase" and distinguish this from the other phases. It is confirmed that the gel forms O/W emulsion spontaneously and diffuses to water phase in the interface of water/gel in the case where the gel contact with an excessive amount of water.

In addition to this, it is found that a homogeneous solution phase which is isotropic optically and is to be considered as bi-continuous type microemulsion can be obtained. The present inventors decide to call this homogeneous phase"isotropic surfactant continuous phase".

EXAMPLE 1

Make-Up Remover

Compositions of Example 1 in accordance with the present invention and Comparative Examples 1 to 3 which are the conventional make-up removers are shown in Table 1 along with the evaluation thereof. Example 1 is a liquid crystal-phase coexisting type make-up remover.

TABLE 1

| Ingredient | Example 1 | Comp. Ex. 1 | Comp. Ex. 2 | Comp. Ex. 3 |
|---|---|---|---|---|
| Purified Water | 25% | 25% | 15% | 42% |
| Polyoxyethylene (5 mol) Dodecyl Ether | 25 | 25 | 25 | 8 |
| Decamethylcyclopentasiloxane | 45 | — | — | 45 |
| Glyceryl 2-Ethyl Hexanoate | — | 45 | 45 | — |
| Ethanol | 5 | 5 | — | 5 |
| Glycerin | — | — | 15 | — |
| State of Phase | LC Coexst. | LC Coexst. | LC Coexst. | Emulsification (Isotropic) |
| Adaptation to Makeup | ○ | Δ | Δ | Δ |
| Oiliness feeling | ○ | Δ | Δ | Δ |
| Effect for Removing Makeup | ⊙ | ○ | ○ | Δ |

Manufacturing Method: Each ingredient was mixed under room temperature.

It is found from Table 1 that the cosmetic preparation of Example 1 which is liquid crystal phase-coexisting type has good adaptation to makeup and favorable feeling of use with no oiliness feeling and is excellent in effect for removing makeup. To the contrary, Comparative Examples 1 and 2 are liquid crystal-phase coexisting type and use the other oily ingredients instead of silicone oil. Nevertheless it is found that these cosmetic preparations are inferior to the cosmetic preparation of Example 1 with respect to adaptation to makeup and oiliness. Comparative Example 2 uses glycerin instead of ethanol in the composition of Comparative Example 1. Also, Comparative Example 3 which is an emulsion composition and do not correspond to one-phase system of liquid crystal-phase type or isotropic surfactant continuous phase type comprises all ingredients, i.e., the nonionic surfactant, the water-soluble substance having a hydroxyl group, the silicone oil and water. Nevertheless, Comparative Example 3 is inferior to Example 1 and the other Comparative Examples with respect to all evaluation items.

EXAMPLE 2

Make-Up Removing Lotion

Compositions of Example 2 in accordance with the present invention and Comparative Examples 4 to 6 which are the conventional make-up removing lotions are shown in Table 2 along with the evaluation thereof. Example 2 is an isotropic surfactant continuous phase type make-up removing lotion.

TABLE 2

| Ingredient | Example 2 | Comp. Ex. 4 | Comp. Ex. 5 | Comp. Ex. 6 |
|---|---|---|---|---|
| Purified Water | 40% | 40% | 53% | — |
| Polyoxyethylene (8 mol) Glyceryl Monoisostearate | 37 | 37 | 37 | 37 |
| Decamethylcyclopentasiloxane | 13 | — | — | 26.5 |
| Glyceryl 2-Ethyl Hexanoate | — | 13 | — | 26.5 |
| Ethanol | 10 | 10 | 10 | 10 |
| State of Phase | Isotropic Surfactant Continuous Phase (One-Phase) | Isotropic Surfactant Continuous Phase (One-Phase) | Micelle Solution (Emulsification) | Reversed Micelle Solution |
| Adaptation to Makeup | ○ | Δ | Δ | ○ |
| Oiliness feeling | ○ | Δ | Δ | X |
| Effect for Removing Makeup | ⊙ | ○ | Δ | ○ |

Manufacturing Method: Each ingredient was mixed under room temperature.

It is found from Table 2 that the cosmetic preparation of Example 2 which is one-phase of isotropic surfactant continues phase type has good adaptation to makeup and favorable feeling of use with no oiliness feeling and is excellent in effect for removing makeup. To the contrary, Comparative Examples 4 which uses the other oil ingredients instead of silicone oil is inferior to Example 2 with respect to adaptation to makeup and oiliness feeling. Comparative Example 5 that does not comprise oil ingredient is inferior to Example 2 with respect to all evaluation items. Also, though Comparative Example 6 which is oil type and does not comprise water has no problem with respect to adaptation to makeup and effect for removing makeup, nevertheless Comparative Example 6 is outstandingly inferior to Example 2 with respect to oiliness.

Then the present inventors have studied the amount of each ingredient.

Amount of Nonionic Surfactant

The amount of the nonionic surfactant has been studied in the system of (A) nonionic surfactant, (B) water-soluble substance having hydroxyl group, (C) silicone oil, and (D) water. The result is shown in Table 3.

TABLE 3

| Ingredient | Test Ex. 1 | Test Ex. 2 | Test Ex. 3 | Test Ex. 4 | Test Ex. 5 | Test Ex. 6 |
|---|---|---|---|---|---|---|
| Purified Water | 42% | 20% | 30% | 15% | 15% | 15% |
| Polyoxyethylene (5 mol) Dodecyl Ether | 8 | 10 | 15 | 50 | 60 | 65 |
| Decamethylcyclopentasiloxane | 45 | 65 | 50 | 30 | 20 | 15 |
| Ethanol | 5 | 5 | 5 | 5 | 5 | 5 |

TABLE 3-continued

| State of Phase | Emulsification Isotropic | LC Coexst. | LC Coexst. | LC Coexst. | LC Coexst. | Reversed Micelle Isotropic |
|---|---|---|---|---|---|---|
| Adaptation to Makeup | Δ | ○ | ○ | ○ | ○ | ○ |
| Oiliness feeling | Δ | ○ | ○ | ○ | ○ | X |
| Effect Removing Makeup | Δ | ○ | ⊙ | ⊙ | ○ | ○ |

From the result as stated above, it is understood that the amount of the nonionic surfactant in the cosmetic preparation of the present invention is 10 to 60 wt %.

Amount of Water-Soluble Substance Having Hydroxyl Group

Then, the amount of the water-soluble substance having a hydroxyl group has been studied in the system of (A) nonionic surfactant, (B) water-soluble substance having hydroxyl group, (C) silicone oil, and (D) water. The result is shown in Table 4.

TABLE 4

| Ingredient | Test Ex. 7 | Test Ex. 8 | Test Ex. 9 | Test Ex. 10 | Test Ex. 11 |
|---|---|---|---|---|---|
| Purified Water | 25% | 25% | 10% | 10% | 10% |
| Polyoxyethylene (5 mol) Dodecyl Ether | 25 | 25 | 25 | 25 | 25 |
| Decamethylcyclopentasiloxane | 49.9 | 49 | 35 | 15 | 5 |
| Glycerin | 0.1 | 1 | 30 | 50 | 60 |

| State of Phase | Emulsification Isotropic | LC Coexst. | LC Coexst. | LC Coexst. | Reversed Micelle Isotropic |
|---|---|---|---|---|---|
| Adaptation to Makeup | Δ | ○ | ○ | ○ | ○ |
| Oiliness feeling | Δ | ○ | ○ | ○ | X |
| Effect for Removing Makeup | Δ | ○ | ⊙ | ○ | ○ |

From the result as stated above, it is understood that the amount of the water-soluble substance having a hydroxyl group in the cosmetic preparation of the present invention is 1 to 50 wt %.

Amount of Silicone Oil

Then, the amount of the silicon oil has been studied in the system of (A) nonionic surfactant, (B) water-soluble substance having hydroxyl group, (C) silicone oil, and (D) water. The result is shown in Table 5.

TABLE 5

| Ingredient | Test Ex.12 | Test Ex.13 | Test Ex.14 | Test Ex.15 |
|---|---|---|---|---|
| Purified Water | 60% | 60% | 30% | 10% |
| Polyoxyethylene (5 mol) Dodecyl Ether | 34.9 | 34 | 25 | 15 |
| Decamethylcyclopentasiloxane | 0.1 | 1 | 40 | 70 |
| Ethanol | 5 | 5 | 5 | 5 |

| State of Phase | Emulsification Isotropic | LC Coexst. | LC Coexst. | LC Coexst. |
|---|---|---|---|---|
| Adaptation to Makeup | Δ | ○ | ○ | ○ |
| Oiliness feeling | Δ | ○ | ○ | ○ |
| Effect for Removing Makeup | Δ | ○ | ⊙ | ○ |

From the result as stated above, it is understood that the amount of the silicone oil in the cosmetic preparation of the present invention is 1 to 70 wt %. Improvement of effect for usability can not be expected in case of compounding more than 70 wt % of the silicone oil.

Amount of Water

The amount of water has been studied in the system of (A) nonionic surfactant, (B) water-soluble substance having hydroxyl group, (C) silicone oil, and (D) water. The result is shown in Table 6.

TABLE 6

| Ingredient | Test Ex.17 | Test Ex.18 | Test Ex.19 | Test Ex.20 | Test Ex.21 |
|---|---|---|---|---|---|
| Purified Water | 5% | 10% | 30% | 60% | 65% |

TABLE 6-continued

| | | | | | |
|---|---|---|---|---|---|
| Polyoxyethylene (5 mol) Dodecyl Ether | 20 | 25 | 25 | 30 | 30 |
| Decamethylcyclopentasiloxane | 70 | 60 | 40 | 5 | 1 |
| Ethanol | 5 | 5 | 5 | 5 | 4 |

| State of Phase | Reversed Micelle Isotropic | LC Coexst. | LC Coexst. | LC Coexst. | Emulsification Isotropic |
|---|---|---|---|---|---|
| Adaptation to Makeup | ○ | ○ | ○ | ○ | Δ |
| Oiliness feeling | X | ○ | ○ | ○ | Δ |
| Effect for Removing Makeup | ○ | ○ | ⊚ | ○ | Δ |

From the result as stated above, it is understood that the amount of water in the cosmetic preparation of the present invention is 10 to 60 wt %.

Accordingly, it is understood that the cosmetic preparation of the present invention comprises (A) 10 to 60 wt % of the nonionic surfactant, (B) 1 to 50 wt % in all of one or more of the water-soluble substance having a hydroxyl group, (C) 1 to 70 wt % of the silicone oil, and (D) 10 to 60 wt % of water and is the composition having a liquid crystal phase and/or an isotropic surfactant continuous phase. Also, it is understood that the liquid crystal composition in accordance with the present invention is approximately within the range of the composition mentioned hereinbefore.

Weight Ratio of Nonionic Surfactant and Water

The weight ratio of (nonionic surfactant/water) has been studied in the system of (A) nonionic surfactant, (B) water-soluble substance having hydroxyl group, (C) silicone oil, and (D) water. The result is shown in Table 7.

TABLE 7

| Ingredient | Test Ex. 22 | Test Ex.23 | Test Ex.24 | Test Ex.25 | Test Ex.26 |
|---|---|---|---|---|---|
| Purified Water | 45% | 33% | 25% | 10% | 8% |
| Polyoxyethylene (5 mol) Dodecyl Ether | 5 | 17 | 25 | 40 | 42 |
| Decamethylcyclopentasiloxane | 45 | 45 | 45 | 45 | 45 |
| Ethanol | 5 | 5 | 5 | 5 | 5 |
| Weight Ratio Nonionic Surfactant/Water | 0.11 | 0.52 | 1.00 | 4.00 | 5.25 |

| State of Phase | Emulsification Isotropic | LC Coexst. | LC Coexst. | LC Coexst. | Reversed Micelle Isotropic |
|---|---|---|---|---|---|
| Adaptation to Makeup | Δ | ○ | ○ | ○ | ○ |
| Oiliness feeling | Δ | ○ | ○ | ○ | X |
| Effect for Removing Makeup | Δ | ○ | ⊚ | ○ | ○ |

From the result as stated above, it is understood that the weight ratio of nonionic surfactant/water in the cosmetic preparation of the present invention is approximately 0.5 to 4.

Next, in addition to the make-up remover, the other examples of the cosmetic preparation in accordance with the present invention are also shown in the following.

EXAMPLE 3

Massage Cream

TABLE 8

| Ingredient | Amount (%) |
|---|---|
| Purified Water | 16 |
| Polyoxyethylene (8 mol) Stearyl Ether | 30 |
| Octamethylcyclotetrasiloxane | 30 |
| Glyceryl 2-Ethyl Hexanoate | 4 |
| Ethanol | 10 |
| Glycerin | 10 |

Manufacturing Method: Each ingredient was mixed with heating and dissolving at 70° C.

EXAMPLE 4

Essence

TABLE 9

| Ingredient | Amount (%) |
|---|---|
| Purified Water | 29.5 |
| Polyoxyethylene (10 mol) Cholesteryl Ether | 15 |
| Decamethylcyclopentasiloxane | 3 |

TABLE 9-continued

| Ingredient | Amount (%) |
| --- | --- |
| 1,3-Butylene Glycol | 50 |
| Sodium Chloride | 2 |
| Carageenan | 0.5 |

Manufacturing Method: After dissolving carageenan to purified water, the other ingredients were mixed to the solution with heating and dissolving at 70° C.

EXAMPLE 5

Make-Up Remover

TABLE 10

| Ingredient | Amount (%) |
| --- | --- |
| Purified Water | 19.8 |
| Polyoxyethylene (5 mol) Dodecyl Ether | 28 |
| Decamethylcyclopentasiloxane | 45 |
| Ethanol | 7 |
| Hydroxyethylcellulose | 0.2 |

Manufacturing Method: After dissolving hydroxyethylcellulose to purified water, the other ingredients were mixed to the solution with heating and dissolving.

EXAMPLE 6

Moisture Cream

TABLE 11

| Ingredient | Amount (%) |
| --- | --- |
| Purified Water | 10 |
| Polyoxyethylene (5 mol) Dodecyl Ether | 40 |
| Decamethylcyclopentasiloxane | 39 |
| Ethanol | 10 |
| Squalane | 1 |

Manufacturing Method: Each ingredient was mixed with dissolving under room temperature.

EXAMPLE 7

Hair Cream

TABLE 12

| Ingredient | Amount (%) |
| --- | --- |
| Polyoxyethylene (10 mol) Glyceryl Monoisostearate | 40 |
| Methylsiloxane 20 cs | 1 |
| Isoparaffin | 20 |
| Cetyl 2-Ethyl Hexanoate | 4 |
| Dipropylene Glycol | 10 |
| Ethanol | 20 |
| Purified Water | 5 |

Manufacturing Method: Each ingredient was mixed with dissolving under room temperature.

The cosmetic preparation of the present invention comprises (A) 10 to 60 wt % of a nonionic surfactant, (B) 1 to 50 wt % in all of one or more of a water-soluble substance having a hydroxyl group, (C) 1 to 70 wt % of a silicone oil, and (D) 10 to 60 wt % of water and has a liquid crystal phase and/or an isotropic surfactant continuous phase. Accordingly, in the case where the cosmetic preparation of the present invention is used as a skin care product, the cosmetic preparation is favorable in adaptation to skin and gives smooth feeling. Further, in the case where the cosmetic preparation of the present invention is used as a make-up remover, the cosmetic preparation is favorable in adaptation to makeup and has high makeup removing effect. Still further, in the case where the cosmetic preparation of the present invention is used as a hair care product, the cosmetic preparation is favorable in adaptation to hair and has favorable feeling of use to provide glossiness to hair.

What is claimed is:
1. A liquid crystal composition which comprises:
   (a) 10 to 60 wt % of a nonionic surfactant;
   (b) 1 to 50 wt % of one or more of water-soluble substances having a hydroxyl group;
   (c) 1 to 70 wt % of a cyclic silicone oil; and
   (d) 10 to 60 wt % of water.
2. A cosmetic preparation which comprises:
   (A) 10 to 60 wt % of a nonionic surfactant;
   (B) 1 to 50 wt % of one or more of water-soluble substances having a hydroxyl group;
   (C) 1 to 70 wt % of a cyclic silicone oil; and
   (D) 10 to 60 wt % of water,
   wherein said cosmetic preparation is mainly comprised of a liquid crystal phase or an isotropic surfactant continuous phase, or a gel-phase, or any combination thereof.
3. The cosmetic preparation according to claim 2, wherein said cosmetic preparation is a skin cosmetic.
4. The cosmetic preparation according to claim 2, wherein said cosmetic preparation is a make-up remover.
5. The cosmetic preparation according to claim 2, wherein at least one of said water-soluble substances having a hydroxyl group is a water-soluble monohydric alcohol.
6. The cosmetic preparation according to claim 2, wherein at least one of said water-soluble substances having a hydroxyl group is a water-soluble polyhydric alcohol.
7. The cosmetic preparation according to claim 2, wherein a ratio of the nonionic surfactant to water (nonionic surfactant/water) is 0.5 to 4 (0.5:4).
8. The cosmetic preparation according to claim 2, wherein said cosmetic preparation is either a one-phase system or a coexisting-phase system of plural phases,
   wherein said one phase system is selected from the group consisting of a gel phase, a liquid crystal phase and an isotropic surfactant continuous phase, and
   wherein said coexisting-phase system comprises a phase selected from the group consisting of a gel phase, a liquid crystal phase and an isotropic surfactant continuous phase.
9. The cosmetic preparation according to claim 8, wherein said cosmetic preparation is the one-phase system of the liquid crystal phase.
10. The cosmetic preparation according to claim 8, wherein said cosmetic preparation is the coexisting-phase system of plural phases comprising the liquid crystal phase.
11. The cosmetic preparation according to claim 8, wherein said cosmetic preparation is the one-phase system of the isotropic surfactant continuous phase.
12. The cosmetic preparation according to claim 8, wherein said cosmetic preparation is the coexisting-phase system of plural phases comprising the isotropic surfactant continuous phase.
13. The cosmetic preparation according to claim 8, wherein said isotropic surfactant continuous phase is formed by associating a surfactant with a coexisting-phase system comprising any one of the gel phase, the liquid crystal phase or other phases.

* * * * *